US011737677B2

(12) United States Patent
Zalevsky et al.

(10) Patent No.: US 11,737,677 B2
(45) Date of Patent: Aug. 29, 2023

(54) SYSTEM AND METHOD FOR USE IN PHOTOPLETHYSMOGRAPHY

(71) Applicant: ContinUse Biometrics Ltd., Tel Aviv (IL)

(72) Inventors: Zeev Zalevsky, Rosh HaAyin (IL); Nisim Nisan Ozana, Rehovot (IL); Javier Garcia, Valencia (ES); Ran Califa, Givataym (IL); Sagi Polani, Tel-Aviv (IL); Moshe Arie Ariel Schwarz, Bnei Brak (IL); Hadar Genish, Petah-Tikva (IL)

(73) Assignee: CONTINUSE BIOMETRICS LTD., Tel Aviv (IL)

( * ) Notice: Subject to any disclaimer, the term of this patent is extended or adjusted under 35 U.S.C. 154(b) by 82 days.

(21) Appl. No.: 16/429,284

(22) Filed: Jun. 3, 2019

(65) Prior Publication Data

US 2019/0374113 A1    Dec. 12, 2019

Related U.S. Application Data

(60) Provisional application No. 62/681,867, filed on Jun. 7, 2018.

(51) Int. Cl.
*A61B 5/026* (2006.01)
*A61B 5/024* (2006.01)
*G01N 21/88* (2006.01)

(52) U.S. Cl.
CPC ........ *A61B 5/0261* (2013.01); *A61B 5/02433* (2013.01); *G01N 21/8806* (2013.01)

(58) Field of Classification Search
CPC . A61B 5/0261; A61B 5/02433; A61B 5/0082; A61B 5/02416; A61B 5/145; A61B 5/02; G01N 21/8806
See application file for complete search history.

(56) References Cited

U.S. PATENT DOCUMENTS

| 2014/0031696 | A1* | 1/2014 | Schmeitz | A61B 5/0077 600/473 |
| 2014/0155759 | A1* | 6/2014 | Kaestle | A61F 7/007 600/479 |
| 2015/0223700 | A1* | 8/2015 | Kirenko | A61B 5/14551 600/476 |
| 2017/0014087 | A1 | 1/2017 | Verkruijsse et al. | |
| 2018/0146870 | A1 | 5/2018 | Shewiesh et al. | |
| 2018/0153455 | A1* | 6/2018 | Guazzi | G06T 7/0012 |

* cited by examiner

*Primary Examiner* — Eric F Winakur
*Assistant Examiner* — Abid A Mustansir
(74) *Attorney, Agent, or Firm* — BROWDY AND NEIMARK, P.L.L.C.

(57) ABSTRACT

A system for use in monitoring application is described. The system comprises a light detection unit and an illumination arrangement. The detection unit is configured for collecting light returning from a selected inspection region for determining variations in collected light intensity. The illumination arrangement comprises one or more light sources configured for providing illumination of a selected wavelength range directed toward said inspection region. Wherein the illumination arrangement is arranged around the detection unit to provide symmetrical illumination conditions with respect to an axis connecting said detection unit and said inspection region.

9 Claims, 3 Drawing Sheets

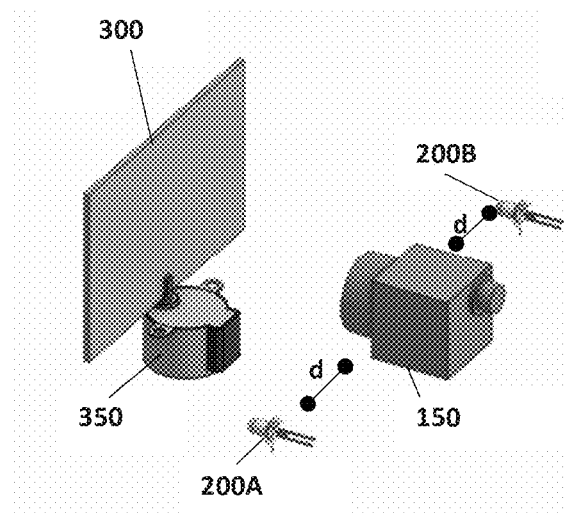
FIG. 3A
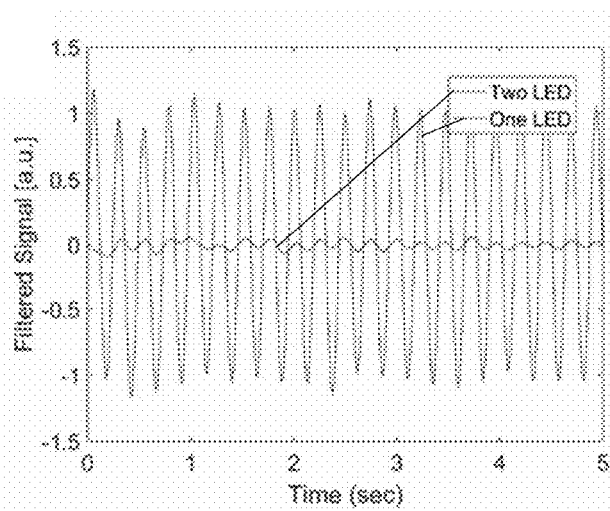
FIG. 3B
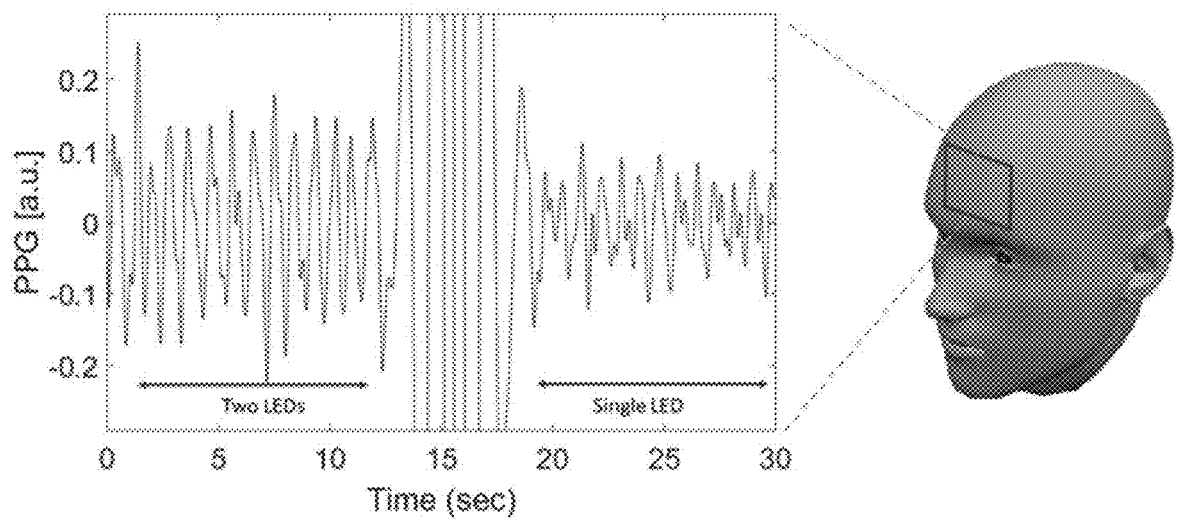
FIG. 4A
FIG. 4B

SYSTEM AND METHOD FOR USE IN PHOTOPLETHYSMOGRAPHY

TECHNOLOGICAL FIELD

The present invention is in the field of optical monitoring of blood flow and is relevant in particular to remote Photoplethysmography (PPG) measurements.

BACKGROUND

Photoplethysmography (PPG) is a low-cost and generally non-invasive technique for measurements of cardiovascular blood volume pulse (BVP). This technique has various clinical applications, and often used in pulse oximeters, vascular diagnostics, and cuff-less blood pressure measurement.

Generally, Photoplethysmography is based on illumination of a region on the skin of a patient and measuring changes in the absorption of that light by the blood underneath that region of the skin. Within the cycle of heart rate, blood is pushed through the arteries in pulses, causing expansion of the arteries. These changes are typically masked by the skin, but observing the changes in the intensity of the reflected/transmitted light enables the detection of such changes in the blood volume, which are associated with the heart rate and pulse volume. Each cardiac cycle is represented as a peak in the light that is reflected or transmitted from that region of the skin, and generally, it appears as a periodic modulation of the detected light intensity.

The conventional Photoplethysmography techniques utilize contact measurement on a selected body part, e.g. fingertip. Such techniques utilize a light source and probe located at high proximity, and generally in direct contact, to the skin. The probe is configured to detect variations in the reflected/transmitted light intensity from the skin. Recently, remote Photoplethysmography (rPPG) techniques are being developed, promising effective PPG measurements while omitting the need for contact probes. Such remote PPG technique utilize ambient light or infrared illumination directed at a region of the body and a detector configured for collecting the reflected light and determining the variations in the intensity of the reflected light.

GENERAL DESCRIPTION

As indicated above, Photoplethysmography measurement provide low-cost and non-invasive technique enabling measurement of cardiac activity including blood volume pulse. While the contact PPG techniques generally provide efficient monitoring, remote PPG techniques generally suffer from noise induced by motion of the patient, making these techniques inaccurate for most health-related applications. Further, additional biomedical measurements may benefit from the present technique enabling optical remote inspection of variations in circulation. For example, pulse oximetry utilizes detection in variations of light intensity in selected one or more wavelength ranges, reflected or transmitted through a tissue. As described below, such measurement may be performed remotely utilizing the present technique with appropriate selection of wavelength of illumination.

Accordingly, present invention provides a technique for use in Photoplethysmography measurements as well as other biomedical monitoring techniques, enabling remote monitoring with increased signal to noise ratio and eliminating, or at least significantly reducing, noise associated with general motion/vibrations of the skin. To this end the present technique utilizes controlled illumination patterns selected and arranged to reduce variations in intensity of the reflected light due to changes in angular orientation of the inspected region. More specifically, the present invention provides an illumination arrangement comprising one or more light source units, that are arranged with respect to path of light collected from the inspection region to minimize variations in intensity of reflected or scattered light that might be caused by movements of the inspected region. The illumination arrangement is configured for compensating illumination variations in accordance with Lambertian backscattering of light from the inspection region.

In some configurations the illumination arrangement may be arranged symmetrically with respect to the detection unit, while the detection unit is configured for collection of light arriving at a selected field of view around an optical axis perpendicular to surface thereof. The symmetrical arrangement of the light source(s) relates to the inspected region to which the detection unit is directed.

Thus, according to a broad aspect, the present invention provides a system comprising a light detection unit and an illumination arrangement; the detection unit is configured for collecting light returning from a selected inspection region for determining variations in collected light intensity; the illumination arrangement comprises one or more light sources configured for providing illumination of a selected wavelength range directed toward said inspection region, wherein the illumination arrangement is arranged around the detection unit to provide symmetrical illumination conditions with respect to an axis connecting said detection unit and said inspection region.

The system may further comprise a control unit configured for receiving input data indicative of collected intensity at a selected sampling rate and for processing the input data for determining data indicative of biomechanical parameters of a patient.

According to some embodiments, the illumination arrangement may comprise a circular light source and wherein said detection unit is located around center of circle defined by the light source.

According to some embodiments, the illumination arrangement may comprise two or more light sources arranged at equal distance in symmetrical arrangement with respect to the detection unit.

According to yet some embodiments of the invention, the illumination arrangement may be configured for illuminating a selected number of two or more regions. Additionally, the detection unit may be configured for collecting light returning from the selected number of two or more regions and for generating for determining variations in collected light intensity for each of said selected number of two or more regions. The system may further comprise a control unit configured for receiving input data comprising said variations in collected light intensity for each of said selected number of two or more regions, and for determining one or more biomedical parameters utilizing averaging of data collected from the two or more regions.

Further, it should be noted that generally the different light sources of the illumination arrangement may be configured for emitting light of slightly different wavelengths within a selected wavelength range. More specifically the illumination arrangement may comprise a plurality of two or more light sources, said plurality of two or more light sources comprises light sources that are configured for emitting light of at least first and second different wavelengths within said selected wavelength range The system may generally be configured as monitoring system for use in optical monitoring of biological parameters. For example, the system may be configured for Photoplethysmography monitoring and preferably for remote Photoplethysmography monitoring. In some specific examples the system described herein may be used for monitoring blood oxygenation levels or other blood relates parameters (e.g. carbon dioxide, glucose level etc.).

Generally, as indicated above, the system of the invention may be used for photoplethysmographic measurements, where variations in intensity of light detection are determined for determining data about blood volume pulse. Alternatively, or additionally, the present technique may be used for detection of blood oxidization levels such as SPO2 measurements or for detection of any other biomedical data.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3A and 3B show respectively experimental model and measurement results of Photoplethysmography technique according to some embodiments of the present invention; and FIGS. 4A and 4B exemplify respectively measurement results and measurement location showing some advantages of the technique according to some embodiments of the present invention.

DETAILED DESCRIPTION OF EMBODIMENTS

Figure 1:
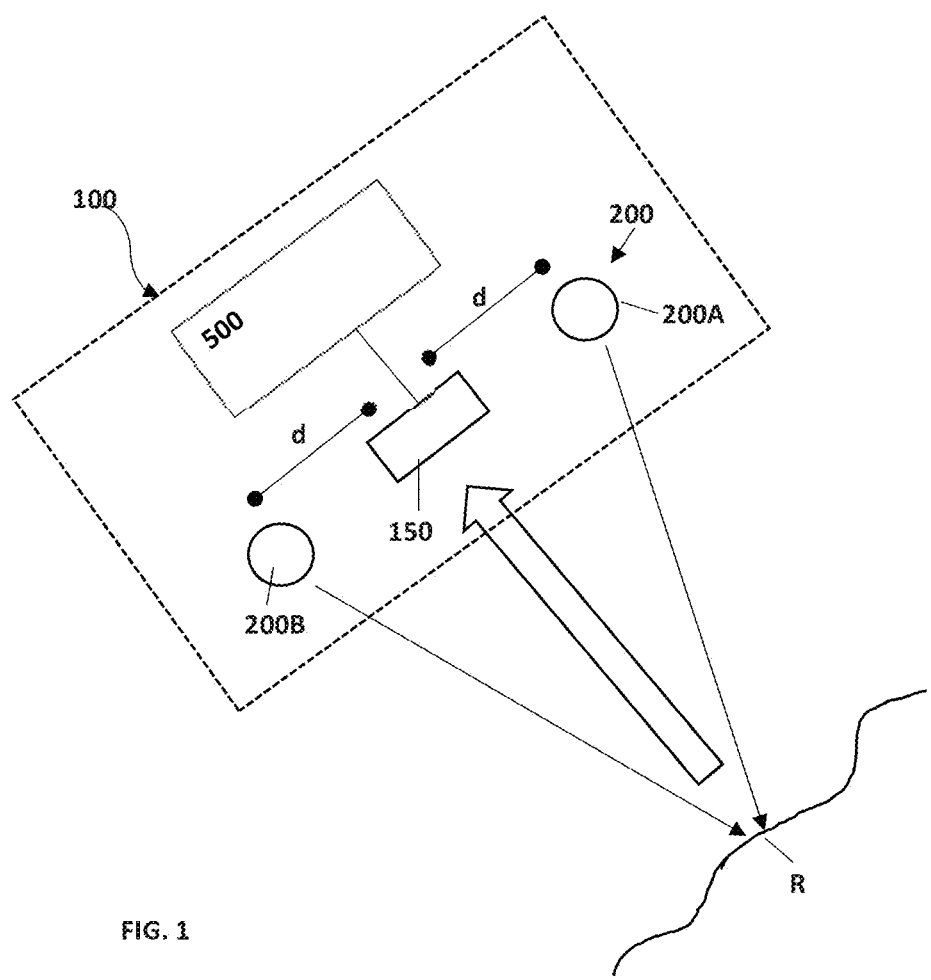
FIG. 1 schematically illustrates a Photoplethysmography system according to some embodiments of the present invention.

As indicated above, the present technique enables remote Photoplethysmography measurements with reduces noise associated with vibrations of the inspected region. Reference is made to FIG. 1 schematically illustrating a system 100 for use in Photoplethysmographic monitoring of an inspection region R. The system includes a detection unit 150 configured for collecting light from the inspection region R (e.g. reflected or scattered light) and illumination arrangement 200 providing selected illumination condition directed onto the inspection region R. The system is also exemplified herein utilizing a control unit 500, connectable at least to the detection unit 150 and configured for operating the system 100 and for receiving and processing collected data for determining output data, e.g. indicative of blood volume pulse and cardiac activity of the patient.

The detection unit 150 generally includes an optical arrangement and one or more detectors and is configured for collecting data on intensity of light arriving from the inspection region R toward the detection unit 150. Changes in intensity of light arriving from the inspection region under constant illumination conditions is typically indicative of variation in light reflection from the inspection region, and may be associated with expansion or contraction of blood vessels at the inspection region.

To eliminate, or at least significantly reduce noise and intensity variations associated with small movements (or vibrations) of the inspection region, the present technique utilizes an illumination unit 200 having two or more light source units, units 200A and 200B are exemplified in FIG. 1, and configured to direct illumination of one or more selected wavelength ranges toward the inspection region R. To provide suitable illumination conditions, the light source units, e.g. 200A and 200B, are arranged symmetrically with respect to the detection unit 150, and preferably with respect to an axis stretching between the detection unit and the inspection region. This arrangement is exemplified in FIG. 1 by distance d between each of the illumination units 200A and 200B and the detection unit 150 to each side.

The illumination arrangement 200 and the spatial configuration of the light source units thereof are selected to compensate for reflection intensity variation due to changes in orientation of the inspection region. The inventors of the present invention have understood that the backscattered light coming from a human skin, of generally any sample, generally follows the Lambertian cosine law at small angles $$I_S = I_L \cdot C \cdot \vec{L} \cdot \vec{N} = I_L \cdot C \cdot \cos(\alpha) \qquad \text{(equation 1)}$$

where $I_S$ is the scattered light intensity, $I_L$ is the intensity of the illumination, L is a normalized vector in the direction of the incoming light, N is the surface normal, C describe the efficiency of the scattering at the given wavelength, historically known as the "color" of the surface, and a is the angle between the light direction and the surface normal.

The light intensity (power) reflected from the surface, in a direction suitable to be collected by the detection unit, is thus sensitive to the relating angles between direction of propagation of light illuminating the surface, the normal to the surface/skin interface from which the scattering light is collected, and the direction of propagation toward the detection unit. Thus, angle variations caused by skin vibrations generate intensity noise affecting the SNR of the detected signal. The use of the illumination arrangement 200 including symmetrically arranged light source units as described herein provides illumination conditions minimizing the angular variation. More specifically, positioning two or more light sources illuminating the inspection region R at opposite angles, provides compensation to angular variation due to small surface tilting.

Figure 2A:
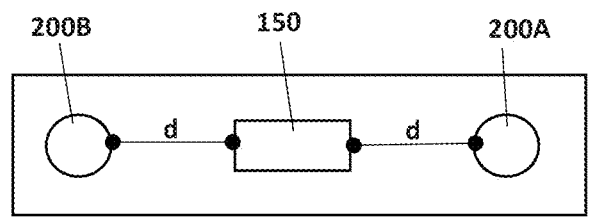
FIGS. 2A to 2D exemplify three arrangements of light source units of the illumination arrangement according to some embodiments of the present invention with respect to the detection unit.
Figure 2B:
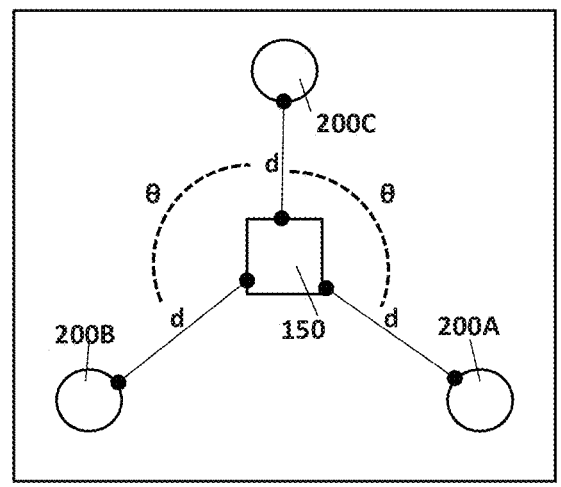
Figure 2C:
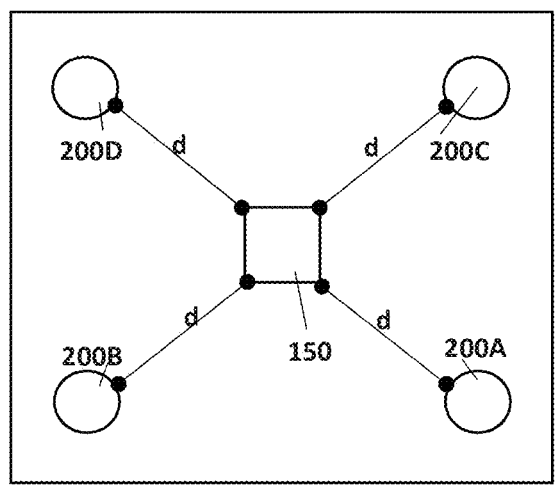
Figure 2D:
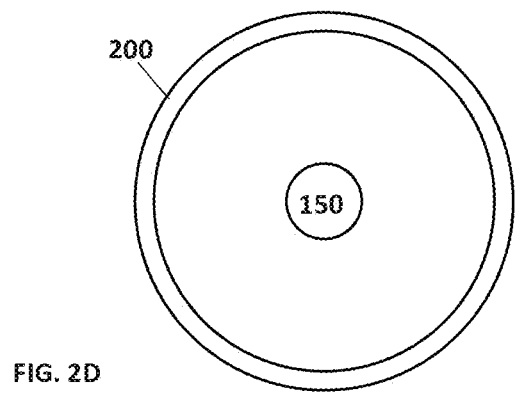

In this connection, reference is made to FIGS. 2A to 2D illustrating examples of illumination arrangement 200 according to some embodiments of the invention. FIG. 2A shows an arrangement of two light sources 200A and 200B arranged symmetrically at equal distances from the detection unit 150. FIG. 2B shows an arrangement of three light source units 200A, 200B and 200C arranged symmetrically with respect to the detection unit 150. FIG. 2C shows an arrangement of 4 light source units 200A to 200D. FIG. 2D shows an arrangement of one circular light source unit 200 positioned such that the circular light source is around the detection unit 150, located at center of the circle. It should be noted that in each of FIGS. 2A to 2C, the light sources 200A to 200D are shown to be in distance d from the detection unit 150. This distance d is equal for light sources in each of these examples to provide symmetry in illumination condition. Further, the distance d may be selected in accordance with number of light sources, illumination intensity and preferred operation distance.

Additionally, light sources 200A to 200C exemplified in FIG. 2B are illustrated to be arranged in selected angular arrangement. More specifically the light sources 200A to 200C are illustrates as having angle θ between them with respect to the detection unit 150. Generally to provide symmetry condition, the angle θ may preferably selected to be 120°.

The symmetry of arrangement of the light sources with respect to the detection unit 150, and generally with respect to axis of light collection stretching between the inspection region and the detection unit 150, provides uniformity of illumination eliminating, or at least significantly reducing variation in reflection intensity due to small vibrations or movements of the inspection region. Generally, the arrangement of the light sources according to the present technique, provides that angular variation of the inspection region to one direction, is associated with variation of relative illumination and reflection angles for two or more light components in different directions.

In some configuration of the system as described herein, the illumination arrangement 200 may be configured for illuminating two or more regions for inspection. For each of the regions, the illumination conditions provide multi-directional illumination having selected symmetry, providing reduced intensity variations associated with vibrations or small movement. Additionally, the detection unit 150 may also be configured for collecting light reflected/scattered from the different regions, generally using two or more corresponding detectors, and for generating corresponding output data. This may allow minimizing noise associated with movements/vibrations of the patient for each region using the illumination arrangement as well as averaging monitored signal from two or more regions of inspection for further reducing additional noise or other measurement interference. Based on high SNR output data the system can thus be used for determining high accuracy biomedical data (PPG, SPO2 etc.).

To evaluate the concept, the inventors have used an experimental model. FIGS. 3A and 3B show an experimental model and measurement results associated with tilting of a screen and determining intensity of light reflected therefrom. The model illustrates in FIG. 3A includes a camera unit used as detection unit 150, two light emitting diodes (LED) light sources 200A and 200B located at equal distances d on two sides of the camera 150, and a rotatable partially reflective screen 300. The screen is located at distance of 50 cm from the camera and the illumination LEDs are positioned at distance of 10 cm on each side of the camera. The LEDs are configured to emit light at 850 nm where one or both LEDs is operated selectively. The screen 300 (also referred at times as surface) was tilted in a periodical manner within a range of 5 degrees back and forth using a stepper motor and a microcontroller 350. The camera 150 was operated to record reflected/scattered light from the surface 300 at 50 frames per second (fps) when the surface is illuminated using one or both of the LEDs. FIG. 3B shows graphs of the collected intensity signals over time. The presented signal was filtered by bandpass filter to show signal portions associated with frequency between 0.3 Hz and 5 Hz to remove white noise and show the tilting of the screen 300. As shown in FIG. 3B the use of single LED (one LED) for illuminating the screen shows high amplitude periodic changes in reflected intensity associated with screen periodic tilting. This is while the use of two illuminating LEDs (two LED) reduces the intensity variations associated with the periodic screen tilting by about an order of magnitude.

Additional verification experiment utilized recording of reflected signals from the forehead of a patient when using one or both of the illumination LEDs. The system is similar to that illustrated in FIG. 3A where the screen is replaced by inspecting a region on forehead of a patient. During the recording the patient was sitting in a natural position while his head was not supported anyway and was free to move. FIGS. 4A and 4B illustrate respectively a graph showing the experimental results (FIG. 4A) and region on the forehead of the patient that was the inspection region (FIG. 4B). FIG. 4A shows collected data with three phases, during the first ten seconds of recorded measurement both LEDs were used for illumination, and in the last ten seconds shown in the figure only one of the LEDs was used. The two measurement portions are separated by noisy period associated with switching off one of the LEDs. The graph of FIG. 4A clearly shows that the PPG signal recorded at the first part of the recording, where both light sources were illuminating the patient forehead, has high resemblance to expected PPG with low noise interference. This is opposed to the measurement portion using single LED where the noise overcomes the expected measurement of PPG signal.

Thus, the present technique provides a system for use in photoplethysmographic measurements enabling reduced noise associated with patient movements. The system utilizes illumination arrangement configured to provide selected illumination conditions that are generally symmetrical with respect to the detection path of the system to thereby reduce Lambertian variation in intensity of collected light.

The invention claimed is:

1. A system comprising: an illuminator for illuminating a selected inspection region with light of a selected wavelength range, and at least one light detector defining a detection path connecting said at least one detector and said selected inspection region and being configured for collecting light returning from the selected inspection region under illumination over time and generating data indicative of detected variations in collected light intensity;
   wherein the illuminator comprises one or more light sources arranged to define multiple illumination paths arranged symmetrically with respect to the detection path, and
   wherein the illuminator is controllably operable to provide simultaneous multi-directional constant illumination of said selected wavelength range of said selected inspection region along said multiple illumination paths under symmetrical illumination conditions with respect to the detection path, thereby providing uniformity of the illumination during collection of the light returning from the selected inspection region along said detection path,
   thereby providing that the detected variations in intensity of light being collected over time from the selected inspection region subjected to the constant illumination under the symmetrical illumination conditions are indicative of variation of light returned from the selected inspection region with compensation of variations of backscattering of illuminating light caused by a change of orientation of the inspection region and reduced variation in reflected intensity caused by movement of the inspection region.

2. The system of claim 1, further comprising a control unit configured for receiving input data indicative of the detected variations in the collected light intensity at a selected sampling rate and for processing the input data for determining data indicative of at least one of the following biomechanical parameters of a patient: PPG, $SpO_2$, heart rate.

3. The system of claim 1, wherein said illuminator comprises a circular light source and wherein said at least one detector is located around a center of a circle defined by the light source.

4. The system of claim 1, wherein said illuminator comprises two or more light sources arranged at equal distance in symmetrical arrangement with respect to the detection path.

5. The system of claim 1, further comprising a control unit configured for receiving and processing input data indicative of said variations in the collected light intensity detected under the symmetrical illumination conditions and being associated with expansion or contraction of blood vessels at the inspection region, and generating output data indicative of cardiovascular blood volume pulse, enabling photoplethysmographic measurements.

6. The system of claim 1, further comprising a control unit configured for receiving and processing input data indicative of said variations in the collected light intensity detected under the symmetrical illumination conditions and being associated with expansion or contraction of blood vessels at the inspection region, and generating output date indicative of $SpO_2$ thereby enabling blood oxidization measurements.

7. The system of claim 1, wherein said illuminator is configured for illuminating a selected number of two or more inspection regions to provide the constant illumination under the symmetrical illumination conditions for each of said two or more inspection regions, and said at least one detector comprises two or more detectors configured for collecting light returning from corresponding two or more of said inspection regions being illuminated and for detecting variations in collected light intensity for each of said selected number of two or more regions.

8. The system of claim 7, comprising a controller configured for receiving input data comprising said variations in collected light intensity for each of said selected number of two or more regions, and for determining one or more biomedical parameters utilizing averaging of data collected from the two or more regions.

9. The system of claim 1, wherein said illuminator comprises a plurality of two or more light sources, said plurality of two or more light sources comprises light sources configured for emitting light of at least first and second different wavelengths within said selected wavelength range.

* * * * *